(12) United States Patent
Heiner

(10) Patent No.: US 6,551,274 B2
(45) Date of Patent: Apr. 22, 2003

(54) CRYOABLATION CATHETER WITH AN EXPANDABLE COOLING CHAMBER

(75) Inventor: Wilfred Peter Heiner, Bakkeveen (NL)

(73) Assignee: Biosense Webster, Inc., Diamond Barr, CA (US)

(*) Notice: Subject to any disclaimer, the term of this patent is extended or adjusted under 35 U.S.C. 154(b) by 113 days.

(21) Appl. No.: 09/753,904

(22) Filed: Jan. 3, 2001

(65) Prior Publication Data

US 2001/0037081 A1 Nov. 1, 2001

Related U.S. Application Data

(60) Provisional application No. 60/185,652, filed on Feb. 29, 2000.

(51) Int. Cl.$^7$ .................................................. A61F 7/12
(52) U.S. Cl. ........................ 604/113; 604/96; 604/97; 604/102; 604/103; 606/20; 606/21; 606/22; 606/23
(58) Field of Search ............................. 604/113, 96.01, 604/97.01, 102.01, 103.01, 102.02; 606/20, 21, 22, 23, 24

(56) References Cited

U.S. PATENT DOCUMENTS

| | | | |
|---|---|---|---|
| 3,125,096 A | | 3/1964 | Antiles et al. |
| 3,712,306 A | * | 1/1973 | Bryne ..................... 128/303.1 |
| 3,924,628 A | | 12/1975 | Droegemueller et al. |
| 4,022,215 A | | 5/1977 | Benson |
| 4,082,096 A | | 4/1978 | Benson |
| 5,224,943 A | * | 7/1993 | Goddard ..................... 606/20 |
| 5,232,445 A | * | 8/1993 | Bonzel ..................... 604/96 |
| 5,281,215 A | | 1/1994 | Milder |
| 5,284,473 A | * | 2/1994 | Calabria ..................... 604/53 |
| 5,287,213 A | | 2/1994 | Zhuang et al. |
| 5,334,154 A | * | 8/1994 | Samson et al. ............. 604/102 |
| 5,370,617 A | * | 12/1994 | Sahota ..................... 604/102 |
| 5,385,548 A | * | 1/1995 | Williams et al. ............. 604/96 |
| 5,413,581 A | * | 5/1995 | Goy ..................... 606/194 |
| 5,423,807 A | | 6/1995 | Milder |
| 5,501,681 A | | 3/1996 | Neuwirth et al. |
| 5,624,392 A | | 4/1997 | Saab |
| 5,807,328 A | * | 9/1998 | Briscoe ..................... 604/96 |
| 5,807,391 A | | 9/1998 | Wijkamp |
| 5,846,235 A | * | 12/1998 | Pasricha et al. ............. 606/23 |
| 5,868,735 A | * | 2/1999 | Lafontaine ..................... 606/21 |
| 5,902,299 A | | 5/1999 | Jayaraman |
| 5,971,979 A | | 10/1999 | Joye et al. |
| 6,014,579 A | * | 1/2000 | Pomeranz et al. ............. 600/374 |
| 6,139,570 A | * | 10/2000 | Saadat et al. ............. 607/105 |
| 6,179,827 B1 | * | 1/2001 | Davis et al. ............. 604/523 |
| 6,283,959 B1 | * | 9/2001 | Lalonde et al. ............. 606/21 |
| 6,355,029 B1 | * | 3/2002 | Joye et al. ............. 606/21 |

FOREIGN PATENT DOCUMENTS

| | | |
|---|---|---|
| EP | 0 407 229 A2 | 1/1991 |
| WO | 94/18896 A1 | 9/1994 |
| WO | 97/48451 A1 | 12/1997 |

\* cited by examiner

*Primary Examiner*—Ira S. Lazarus
*Assistant Examiner*—Tu Cam Nguyen
(74) *Attorney, Agent, or Firm*—Henry W. Collins

(57) ABSTRACT

A cryoablation catheter having an expandable cooling chamber in which the cooling fluid, preferably a gas, serves to expand the expandable cooling chamber while simultaneously cooling the chamber.

7 Claims, 2 Drawing Sheets

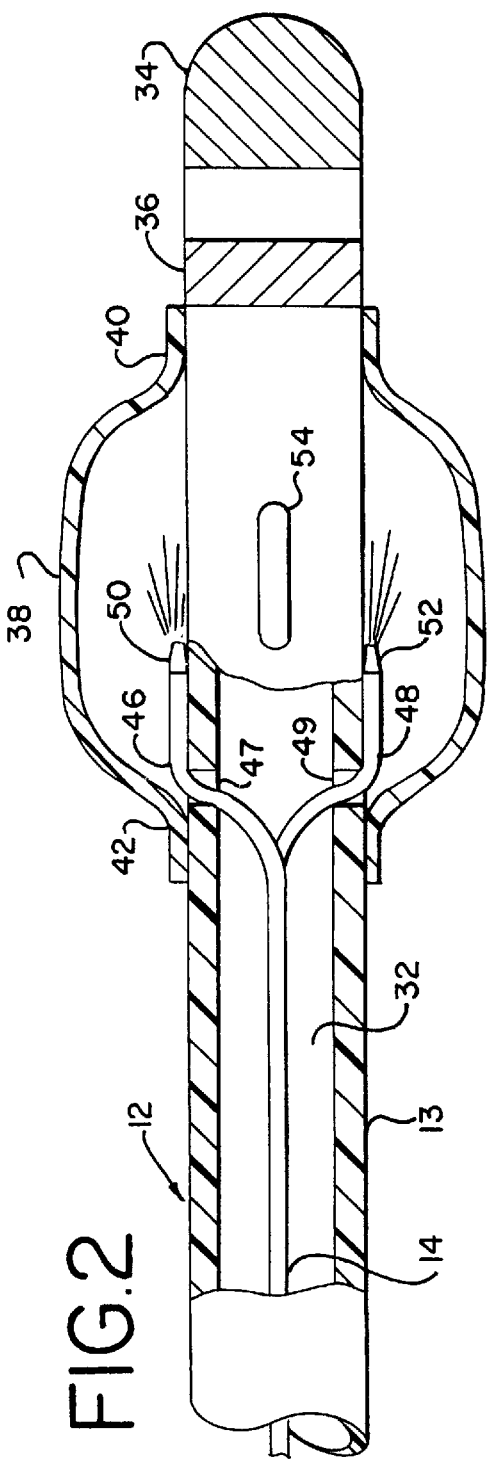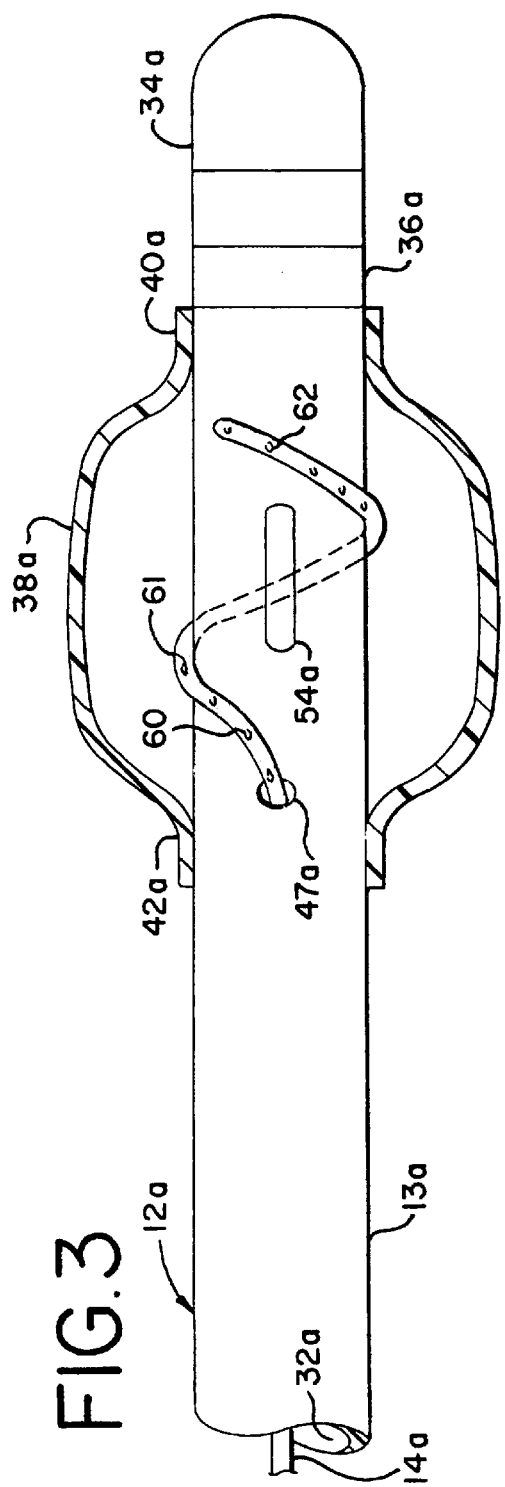

CRYOABLATION CATHETER WITH AN EXPANDABLE COOLING CHAMBER

This application claims the benefit of Provisional application Ser. No. 60/185,652, filed Feb. 29, 2000.

BACKGROUND OF THE INVENTION

1. Field of the Invention

The present invention relates to a cryoablation catheter, and more particularly to a cryoablation catheter for creating long lesions.

2. Description of the Prior Art

Many medical procedures are performed using minimally invasive surgical techniques wherein one or more slender implements are inserted through one or more small incisions into a patient's body. With respect to ablation, the surgical implement may include a rigid or flexible structure having an ablation device at or near its distal end that is placed adjacent to the tissue to be ablated. Radio frequency energy, microwave energy, laser energy, extreme heat, or extreme cold may be provided by the ablation device to destroy the tissue.

With respect to cardiac procedures, a cardiac arrhythmia may be treated through selective ablation of cardiac tissue to eliminate the source of the arrhythmia. A popular minimally invasive procedure, radio frequency (RF) catheter ablation, includes a preliminary step of conventional electrophysiology mapping followed by the creation of one or more ablated regions (lesions) in the cardiac tissue using RF energy. Multiple lesions are frequently required because the effectiveness of each of the lesion sites can not be predetermined with exactness due to limitations of conventional mapping. Often, five lesions, and sometimes as many as twenty lesions may be required before a successful result is attained.

Deficiencies of radio-frequency ablation devices and techniques have been overcome by ice mapping prior to creating lesions, as taught by U.S. Pat. Nos. 5,423,807; 5,281,213 and 5,281,215. However, even though combined cryogenic mapping and ablation devices permit greater certainty and less tissue damage than RF devices and techniques, both the cryogenic and the RF devices are configured for spot or roughly circular tissue ablation.

Spot tissue ablation is acceptable for certain procedures. However, other procedures can be more therapeutically effective if multiple spot lesions are made along a predetermined line, or a single elongate or linear lesion is created in a single ablative step. Radio-frequency ablation devices are known to be able to create linear lesions by dragging the ablation tip along a line while the ablation electrode is energized.

One problem associated with presently existing cryoablation catheters is that the outside dimensions of the cooling chamber must be limited by the size of the vessel. In other words, the outside diameter of the cooling chamber must be slightly smaller than the inside diameter of the vessel in order to permit passage of the cooling chamber through the vessel. Such small cooling chambers are relatively inefficient. It would be far better to have a cryoablation catheter with a large gas expansion chamber in order to increase the cooling efficiency of the device, however, large chambers may not be used within the rather small blood vessels of the human body.

SUMMARY OF THE INVENTION

The present invention provides a cryogenic ablation system including a cryoablation catheter which is particularly well suited for creating elongated lesions.

In accordance with one aspect of the present invention, there is provided a cryoablation catheter which includes an outer tubular member capable of insertion into the vessels of the body. An expandable cooling chamber, which preferably takes the form of a distendable balloon is disposed at the distal end of the outer tubular member. An inner tubular member is disposed within the outer tubular member and extends through a passageway in the wall of the outer tubular member. The inner tubular member serves to carry a cooling fluid to the interior of the expandable cooling chamber. A fluid expansion nozzle is disposed on the distal end of the inner tubular member. Preferably the fluid expansion nozzle takes the form of a Joule-Thompson nozzle. By applying a cooling fluid to the inner tubular member it is possible to expand the expandable cooling chamber while simultaneously cooling the chamber.

In accordance with another aspect of the present invention the fluid expansion nozzle takes the form of a Joule-Thompson fluid expansion nozzle. In addition, the cooling fluid preferably takes the form of a gas which, when allowed to expand, provides cooling at a temperature sufficient to cause cryoablation to occur at the surface of the expandable cooling chamber. One such gas suitable for this purpose is liquid nitrogen.

In accordance with still another aspect of the present invention, the inner tubular member extends through a passageway in the wall of the outer tubular member and the distal end of the inner tubular member is helically wrapped around the outer periphery of the outer tubular member at a position within the expandable cooling chamber. A plurality of holes extend through the wall along the distal portion of the inner tubular member and serve as exit ports for the cooling gas. This embodiment, applying a cooling fluid, such as liquid nitrogen, to the inner tubular member is possible to expand the expandable cooling chamber while simultaneously cooling the chamber.

In accordance with still another embodiment of the present invention, a cryoablation catheter includes a distal mapping electrode which is mounted on the distal tip of the outer tubular member in order to provide measurements of electrical signals within the chamber of the heart. These electrical signals generated at various locations within the heart serve to map electrical potentials within the heart. In addition, the cryoablation catheter may also include a second intermediate mapping electrode which is mounted on the outer tubular member and is disposed between the distal electrode and the expandable cooling chamber in order to provide a bipolar mapping function.

Accordingly, the cryoablation catheter system incorporates an expandable cooling chamber. The cooling chamber takes the form of distendable balloon which is disposed at the distal end of a catheter and also includes one or more tubes for delivering a cryogenic fluid into the expandable cooling chamber in order to expand the chamber to a desired size and to cause cryogenic cooling to occur within the chamber. By varying the pressure differential between the fluid entering the cooling chamber and pressure exiting the chamber it is possible to vary or control the size of the chamber. The same cryogenic fluid which is used to expand the cooling chamber is also used to create a cooling effect within the chamber, preferably by the use of a Joule-Thompson nozzle, positioned within the chamber. In another embodiment, the cryogenic fluid may be applied to the interior of the balloon by use of a tube which is helically wrapped around the catheter body beneath the balloon in which case the tube includes a plurality of side holes which extend along the tube for injecting the fluid into the cooling chamber.

The main advantage of the present invention is that the cooling chamber of this device may be deflated, or collapsed, prior to the insertion of the chamber into a vessel of the body. Once the chamber has been placed at a location where ablation is to occur, a gas such as nitrous oxide may be applied to the cooling chamber to thereby cause the chamber to expand to a point where it comes into contact with surrounding tissue. Simultaneously, the cooling gas may be injected into the expanded chamber to thereby cool the interior of the chamber, as well as the surface of the chamber itself to thereby cool adjacent tissue. As the adjacent tissue becomes sufficiently cool, this tissue will eventually freeze and ablation of such tissue will occur. Preferably, during this cooling cycle, the balloon or expansion chamber will become attached to the tissue in order to maintain the cooled surface in contact with the tissue.

Accordingly, with this device, it is possible for a physician to freeze larger surface areas, or alternatively longer surface distances, by use of the expandable chamber.

These and other objects of the present invention will become more apparent when considered in view of the following description of a preferred embodiment of the present invention.

BRIEF DESCRIPTION OF THE DRAWINGS

Further properties, advantages and measures according to the present invention will be explained in greater detail in the description of a preferred embodiment, with reference to the attached figures in which:

FIG. 2 illustrates in detail the distal portions of a cryoablation catheter according to the present invention; and, FIG. 3 illustrates in detail another embodiment of a cryoablation catheter according to the present invention.

DESCRIPTION OF THE PREFERRED EMBODIMENT

Figure 1:
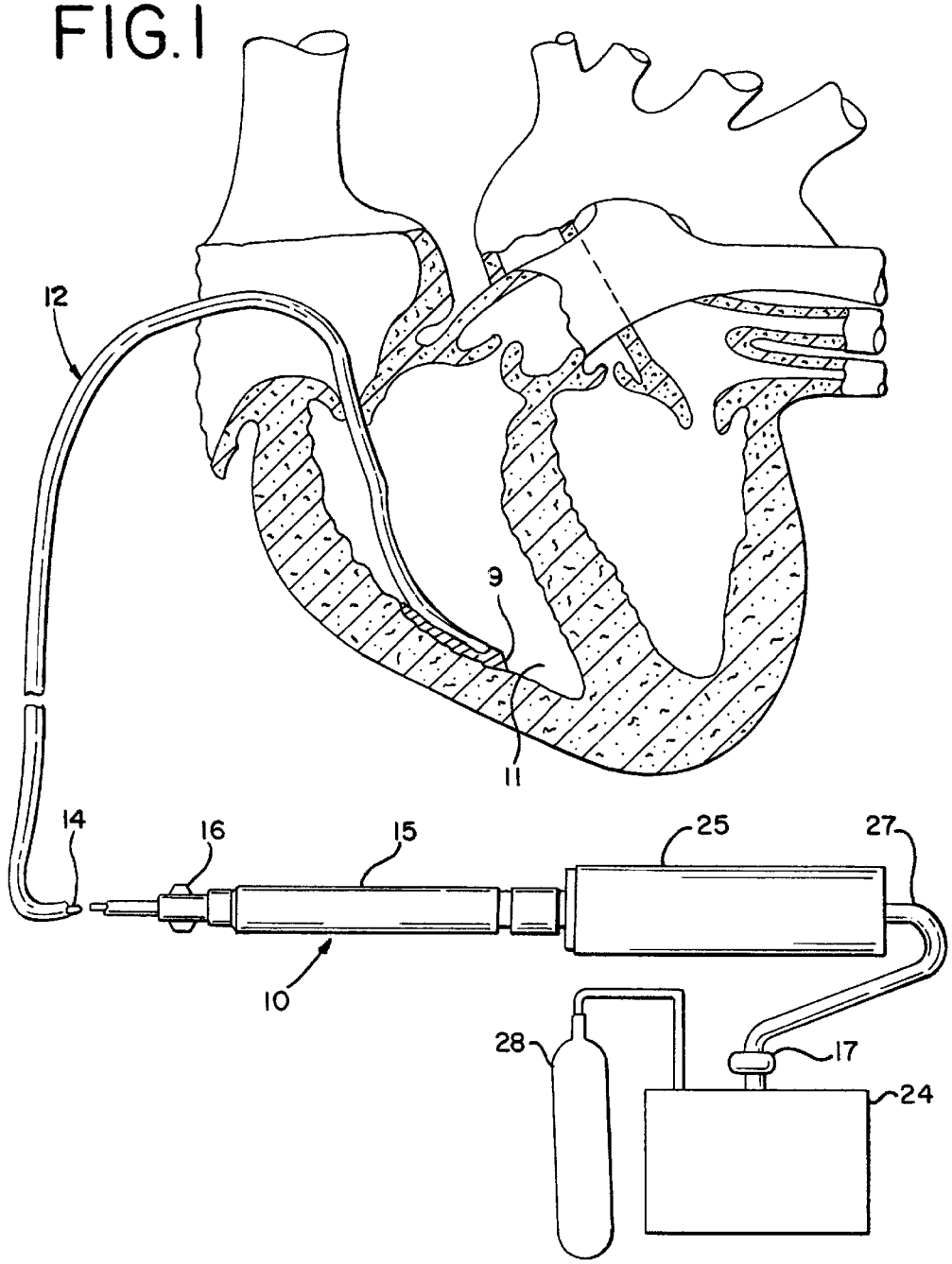
FIG. 1 is a schematic view of a cryoablation system including a cryoablation catheter according to the present invention shown with respect to a human heart.

FIG. 1 illustrates one embodiment of a cryoablation catheter system 10 according to the present invention which includes a catheter 12. The catheter 12 comprises an outer body 13, an inner body 14, a handle 15 and a control knob 16. The control knob 16 is movable in the axial direction in relation to the handle 15 in such a way that the distal tip of the catheter 12 is deflectable.

The handle 15 is connected to a heat exchanger 25, which is in turn coupled through a connecting tube 27 to a control unit 24. A control valve 17 is disposed in the connecting tube 27 and serves to control the flow of gas from a gas cylinder 28, preferably containing $N_2O$. By way of an alternative, gases other than $N_2O$ may be used for this purpose.

The valve 17 constitutes the control means with which the flow of $N_2O$ through the inner body 14 is regulated. The pressure depends on the intended effect of the cryoablation at the distal tip of the catheter 12.

The tip at the distal end of the catheter 12 may also be provided with other measurement equipment to determine the position of the nozzle 50 for instance. Examples of such measuring equipment are marking rings which are recognizable when using imaging techniques like MRI or when using x-ray radiation.

In the situation illustrated schematically in FIG. 1, the distal end of the catheter 12 has been introduced into a chamber of the heart 11 and advanced to a position where tissue 9 is located which is suitable for ablation. This device could also be used in a vein or at any other locations within the body.

FIG. 2 generally illustrates in detail one embodiment of the distal section of the catheter 12 which includes the flexible catheter outer body 13 having a lumen 32 extending therethrough. The distal tip of the catheter outer body 13 is sealed off by a conductive dome electrode 34 which is in turn electrically connected through conductor wires (not shown) back to the proximal end of the catheter 12. Also, a ring electrode 36 is positioned around the outer circumference of the catheter outer body 13 at a position slightly proximal of the dome electrode 34.

As illustrated, an expandable balloon is disposed around the catheter outer body 13 at a position slightly proximal of the ring electrode 36. More particularly, the balloon, which preferably takes the form of a distendable balloon, includes distal and proximal legs 40, 42 which are bonded around the circumference of the catheter outer body 13 by use of an adhesive material.

In addition, a tubular inner body 14 for carrying a fluid extends through the lumen 32 of the catheter outer body 13 to a location proximal to the balloon 38 at which point the inner body 14 is bifurcated to form two separate tubes 46, 48 which extend through passageways 47, 49 in the side wall of the catheter outer body 13 and into the area enclosed by the balloon 38. The tubes 46, 48 are provided with nozzles, 50, 52, which preferably take the form of Joule-Thompson fluid expansion nozzles, for expanding the fluid to thereby cause cooling to occur.

The catheter also includes a fluid return aperture 54 for returning the fluid, once expanded, back through the catheter lumen 32 to the proximal end of the catheter 12. It is an object of the present invention to provide a cryoablation catheter with a gas expansion, or cooling chamber, which may be expanded to a desired dimension. Accordingly, by controlling the amount of pressure applied through the inner body 14 and through the Joule-Thompson nozzles 50, 52, relative to the pressure of the fluid exiting the balloon, it is possible to either increase or decrease the outer diameter of the gas expansion chamber formed by the balloon 38 while simultaneously applying cooling fluid to the balloon 38.

FIG. 3 generally illustrates in detail another embodiment of the distal section of the catheter 12a which includes a flexible catheter outer body 13a having a lumen 32a extending therethrough. The distal tip of the catheter outer body 13a is sealed off by a conductive dome electrode 34a which is in turn electrically connected through conductor wires (not shown) back to the proximal end of the catheter 12a. Also, a ring electrode 36a is positioned around the outer circumference of the catheter outer body 13a at a position slightly proximal of the dome electrode 34a.

As illustrated, an expandable balloon is disposed around the catheter outer body 13a at a position slightly proximal of the ring electrode 36a. More particularly, the balloon which preferably takes the form of a distendable balloon includes distal and proximal legs 40a, 42a which are bonded around the circumference of the catheter outer body 13a, preferably by use of an adhesive material.

In addition, a tubular inner body 14a for carrying a fluid extends through the lumen 32a of the catheter outer body 13a to a location proximal to the balloon 38a at which point the inner body 14a extends through a passageway 47a in the side wall of the catheter outer body 13a and into the area enclosed by the balloon 38a and is helically wrapped around the outside of the catheter outer body 13a. A plurality of side holes 60, 61, 62 extend through the wall of this distal portion of the inner body 14a which serve to inject the cryogenic fluid into the balloon 38a. The catheter also includes a fluid return aperture 54a for returning the fluid, once expanded, back through the catheter lumen 32a. Accordingly, by controlling the amount of pressure applied through the inner body 14a and through the side holes in the distal portion of the inner body 14a relative to the pressure of the fluid exiting the balloon, it is possible to either increase or decrease the outer diameter of the gas expansion chamber formed by the balloon 38a while simultaneously applying cooling fluid to the balloon 38a.

As indicated, the gas expansion chamber preferably takes the form of a distendable balloon made of a polymeric material, such as nylon, but may be fabricated from numerous other polymeric or metallic materials so long as these materials exhibit the characteristics of being able to expand upon receiving an internal pressure and of being able to withstand the very low temperatures required in the cryoablation process.

The catheter device according to the invention is generally intended to be used to ablate surface tissue inside the heart, or in blood vessels adjacent to the heart, such as the pulmonary vein, but may be used to ablate tissue at any location within the body.

Because of the relatively high heat resistance coefficient of the material of which the inner body 14 has been made, the pre-cooled fluid will at the most absorb only little heat from the surroundings.

It should be noted that only two possible embodiments of the present invention have been illustrated. Other embodiments are possible as well. The heat exchanger 25 for instance may be integrated into the handle 15. The inner body 14a may take the form of an integral lumen extended within the outer body 13a. Alternatively, the balloon 38a may take the form of a distendable or non-distendable polymeric balloon or may be formed from any flexible, fluid-impervious material.

These modifications would be apparent to those having ordinary skill in the art to which this invention relates and are intended to be within the scope of the claims which follow.

That which is claimed is:

1. A cryoablation catheter comprising:

an elongated flexible outer tubular member;

an expandable cooling chamber mounted on the distal end of the outer tubular member;

an inner tubular member extending throughout the length of the outer tubular member and being in fluid communication with the interior of the expandable cooling chamber, said tubular member having a proximal end adapted to be coupled to a source of cryoablation fluid;

a fluid expansion nozzle disposed on the distal end of the inner tubular member so that when a cooling fluid is supplied to the proximal end of the inner tubular member the fluid is caused to expand at the nozzle to thereby simultaneously cause the cooling chamber to expand and cause cooling to occur within the cooling chamber;

wherein the elongated outer tubular member includes a distal end and a lumen which extends from the proximal end to substantially the distal end of the outer tubular member, a passageway extends from the lumen of the outer tubular member to the interior of the expandable cooling chamber, and said inner tubular member extends through the lumen of the outer tubular member and through said passageway into the interior of the expandable cooling chamber.

2. A cryoablation catheter as defined in claim 1 wherein said fluid expansion nozzle takes the form of a Joule-Thompson fluid expansion nozzle.

3. A cryoablation catheter as defined in claim 2 wherein the proximal end of said inner tubular member is coupled to a source of cooling gas.

4. A cryoablation catheter as defined in claim 3 wherein said cooling gas is nitrous oxide.

5. A cryoablation catheter as defined in claim 1 which includes a distal mapping electrode mounted on the distal end of the outer tubular member.

6. A cryoablation catheter as defined in claim 4 which includes an intermediate mapping ring electrode mounted on the outer tubular member and positioned between the distal mapping electrode and the expandable cooling chamber.

7. A cryoablation catheter comprising:

an elongated flexible outer tubular member;

an expandable cooling chamber mounted on the distal end of the outer tubular member;

said elongated outer tubular member having proximal and distal ends and includes a lumen which extends from the proximal end to substantially the distal end of the outer tubular member, and a passageway which extends from the lumen of the outer tubular member to the interior of the distal cooling chamber;

an inner tubular member extends through the lumen of the outer tubular member and through said passageway and into the interior of the expandable cooling chamber and is helically wrapped about a periphery of the outer tubular member at a location within the interior of the expandable cooling chamber; and, said inner tubular member having a distal portion and having multiple fluid holes along the distal portion of the inner tubular member so that cooling fluid is caused to expand at these multiple holes to thereby simultaneously cause the cooling chamber to expand and to cause cooling to occur within the cooling chamber.

* * * * *